United States Patent
Hinds

[11] Patent Number: 6,039,568
[45] Date of Patent: Mar. 21, 2000

[54] TOOTH SHAPED DENTAL IMPLANTS

[76] Inventor: Kenneth F. Hinds, 4 Costa Del Sol, Monarch Beach, Calif. 92629

[21] Appl. No.: 09/088,911

[22] Filed: Jun. 2, 1998

[51] Int. Cl.[7] .................................................. A61C 8/00
[52] U.S. Cl. ......................................... 433/175; 433/173
[58] Field of Search ..................................... 433/172, 173, 433/174, 175 OR, 176, 201.1

[56] References Cited

U.S. PATENT DOCUMENTS

| | | | |
|---|---|---|---|
| 4,185,383 | 1/1980 | Heimke et al. | 433/173 |
| 4,252,525 | 2/1981 | Child | 433/173 |
| 4,293,302 | 10/1981 | Hassler et al. | 433/173 |
| 4,531,916 | 7/1985 | Scantlebury et al. | 433/173 |
| 4,722,688 | 2/1988 | Lonca | 433/173 |
| 4,768,956 | 9/1988 | Kurpis | 433/173 |
| 4,960,381 | 10/1990 | Niznick | 433/174 |
| 4,997,383 | 3/1991 | Weiss et al. | 433/176 |
| 5,006,068 | 4/1991 | Lee et al. | 433/169 |
| 5,007,835 | 4/1991 | Valen | 433/174 |
| 5,061,181 | 10/1991 | Niznick | 433/174 |
| 5,078,607 | 1/1992 | Niznick | 433/174 |
| 5,100,323 | 3/1992 | Friedman et al. | 433/173 |
| 5,145,372 | 9/1992 | Daftary et al. | 433/173 |
| 5,174,755 | 12/1992 | Fukuda | 433/173 |
| 5,199,873 | 4/1993 | Schulte et al. | 433/173 |
| 5,209,659 | 5/1993 | Friedman et al. | 433/173 |
| 5,246,370 | 9/1993 | Coatoam | 433/173 |
| 5,316,476 | 5/1994 | Krauser | 433/173 |
| 5,344,457 | 9/1994 | Pilliar et al. | 433/174 |
| 5,376,004 | 12/1994 | Mena | 433/173 |
| 5,378,152 | 1/1995 | Elia | 433/173 |
| 5,399,090 | 3/1995 | Padros-Fradera | 433/173 |
| 5,425,639 | 6/1995 | Anders | 433/169 |
| 5,427,526 | 6/1995 | Fernandes | 433/173 |
| 5,431,567 | 7/1995 | Daftary | 433/172 |
| 5,470,230 | 11/1995 | Daftary et al. | 433/174 |
| 5,489,210 | 2/1996 | Hanosh | 433/173 |
| 5,492,470 | 2/1996 | Anders | 433/169 |
| 5,533,898 | 7/1996 | Mena | 433/173 |
| 5,564,925 | 10/1996 | Shampanier | 433/173 |
| 5,571,016 | 11/1996 | Ingber et al. | 433/173 |
| 5,584,693 | 12/1996 | Nishihara | 433/169 |
| 5,601,429 | 2/1997 | Blacklock | 433/174 |
| 5,607,480 | 3/1997 | Beaty | 623/16 |
| 5,611,688 | 3/1997 | Hanosh | 433/174 |
| 5,636,989 | 6/1997 | Somborac et al. | 433/173 |
| 5,658,146 | 8/1997 | Kisielewski et al. | 433/172 |
| 5,695,335 | 12/1997 | Haas et al. | 433/173 |
| 5,695,336 | 12/1997 | Lazzara et al. | 433/173 |
| 5,702,346 | 12/1997 | Lazzara et al. | 433/173 |
| 5,704,788 | 1/1998 | Milne | 433/173 |
| 5,709,547 | 1/1998 | Lazzara et al. | 433/174 |
| 5,725,377 | 3/1998 | Lemler et al. | 433/173 |
| 5,727,943 | 3/1998 | Beaty et al. | 433/174 |
| 5,749,732 | 5/1998 | Sendax | 433/174 |

FOREIGN PATENT DOCUMENTS

| | | | |
|---|---|---|---|
| 1958338 | 6/1970 | Germany | 433/173 |

*Primary Examiner*—John J. Wilson
*Attorney, Agent, or Firm*—Thomas I. Rozsa; Tony D. Chen; Jerry Fong

[57] ABSTRACT

A complete truly anatomical dental implant system to replace missing teeth in both the maxillary and mandibular arch. The primary uniqueness of the present invention is in the creation of a unique tooth shaped dental implant that is placed into the jawbone. In addition, the present invention involves and exposes a new procedure, method and apparatus for creating a truly tooth shape cavity into the jawbone which matches the unique tooth shaped implant, thereby providing stability of the implant at placement. Thirdly, the present invention exposes a special cutting tool bit tip that is used in a vibrating and/or oscillating action to produce a hole in the bone that matches the chosen tooth shaped implant. The tooth shaped implant is essentially tapered and triangularly shaped for anterior teeth and some cuspid teeth. The tooth shaped implant is essentially tapered oval-shaped for bicuspid teeth, cuspid teeth and molar teeth. The oval-shaped implant can also be used sideways in many locations throughout the mouth. The tooth shaped implant is essentially tapered oval-rectangular shaped for molar teeth.

24 Claims, 5 Drawing Sheets

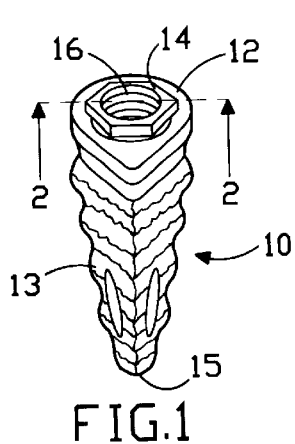
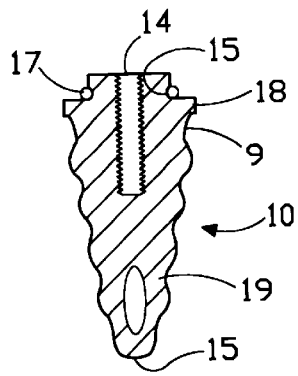
FIG.1  FIG.2
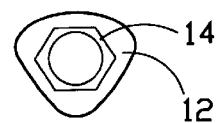
FIG.3
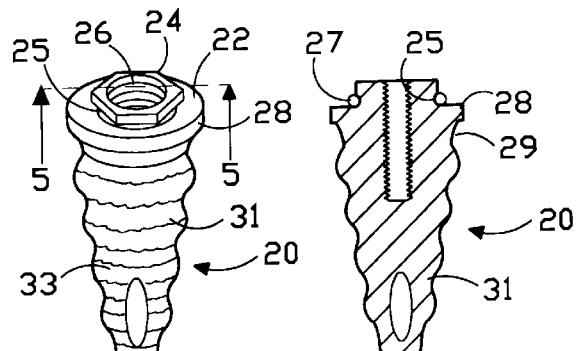
FIG.4  FIG.5
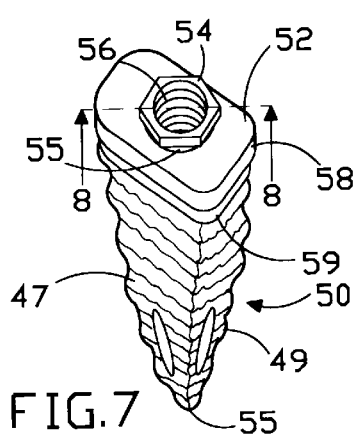
FIG.7
FIG.6
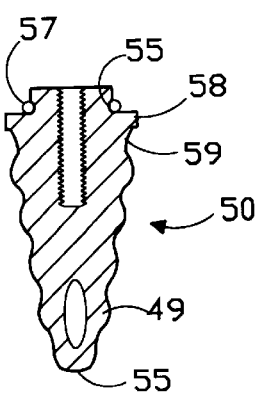
FIG.8
FIG.9

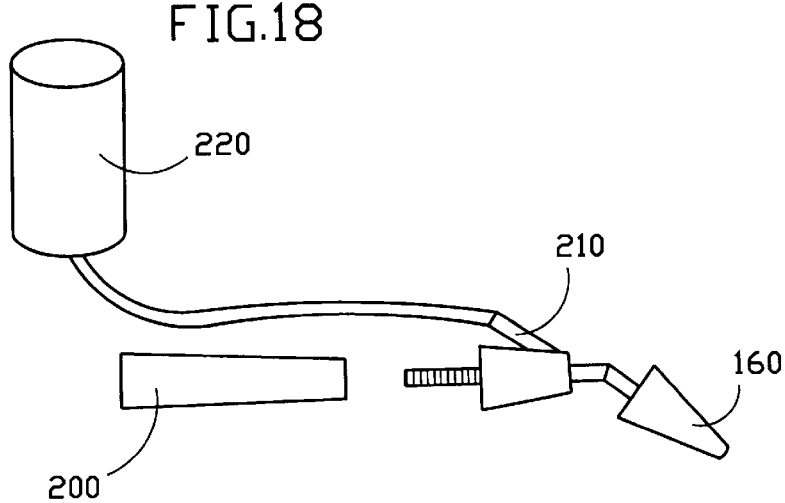
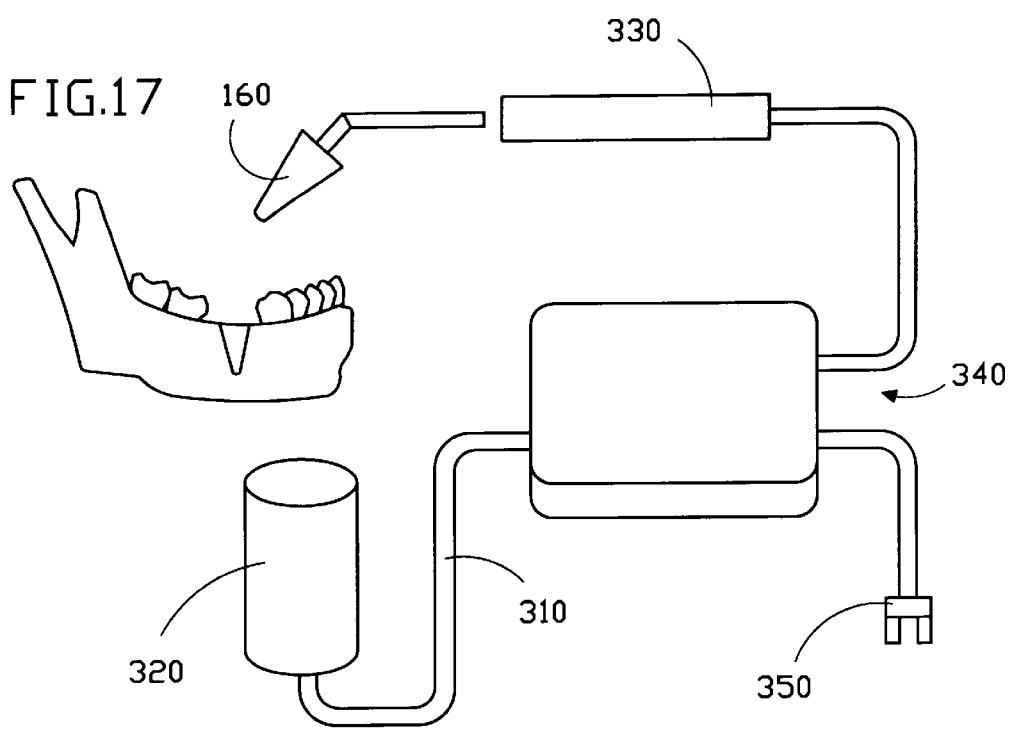

TOOTH SHAPED DENTAL IMPLANTS

BACKGROUND OF THE INVENTION

1. Field of the Invention

The present invention relates generally to the field of dental implants and in particular to the creation of a novel dental implant having tissue implant profiles similar to those of a natural tooth and its surrounding gingiva to thereby create a substantially improved fit between the implant and the tooth restoration analogue, which fit improves both cosmetic appearance and functional utilization.

2. Description of the Prior Art

In the prior art, dental implants that bore into bone to support a prosthesis (i.e. tooth) have been round in shape. Teeth are not round but have distinctive shapes, essentially tapered—triangular for anterior (front), and essentially tapered—oval for posteriors (back).

Over the past decade there have been numerous improvements in the field of dental implants. The improvements have concentrated on improvement to the healing cap and abutment portions of the implant. The inventor is aware of the following prior art patents in this field:

1. U.S. Pat. No. 5,246,370 issued to Coatoam on Sep. 21, 1993 for DENTAL IMPLANT METHOD (hereafter the "'370 patent").
2. U.S. Pat. No. 5,427,526 issued to Fernandes on Jun. 27, 1995 for DENTAL IMPLANT AND DENTISTRY IMPLANT METHOD (hereafter the "'526 patent").
3. U.S. Pat. No. 5,378,152 issued to Elia on Jan. 3, 1995 for METHOD AND APPARATUS FOR INSTALLATION OF DENTAL IMPLANT (hereafter the "'152 patent).
4. U.S. Pat. No. 5,209,659 issued to Friedman et al. on May 11, 1993 for METHOD FOR INSTALLING A DENTAL IMPLANT" (hereafter the "'659 patent").
5. U.S. Pat. No. 5,078,607 issued to Niznick on Jan. 7, 1992 for DENTAL IMPLANT INCLUDING PLURAL ANCHORING MEANS (hereafter the "'607 patent").
6. U.S. Pat. No. 4,960,381 issued to Niznick on Oct. 2, 1990 for SCREW-TYPE DENTAL IMPLANT ANCHOR (hereafter the "'381 patent").
7. U.S. Pat. No. 5,061,181 issued to Niznick on Oct. 29, 1991 for DENTAL IMPLANT INCLUDING PLURAL ANCHORING MEANS (hereafter the "'181 patent").
8. U.S. Pat. No. 5,571,016 issued to Ingber et al. on Nov. 5, 1996 for DENTAL IMPLANT SYSTEM (hereafter the "'016 patent").
9. U.S. Pat. No. 5,470,230 issued to Daftary et al. on Nov. 28, 1995 for ANATOMICAL DENTAL PLANT WITH EXPANDABLE ROOT (hereafter the "'230 patent").
10. U.S. Pat. No. 5,145,372 issued on Sep. 8, 1992 to Daftary et al. for ANATOMICAL RESTORATION DENTAL IMPLANT SYSTEM WITH REINFORCED HEALING CAP AND ABUTMENT (hereafter the "'372 patent").
11. U.S. Pat. No. 5,431,567 issued to Daftary on Jul. 11, 1995 for ANATOMICAL RESTORATION DENTAL IMPLANT SYSTEM WITH INTERLOCKABLE VARIOUS SHAPED HEALING CAP ASSEMBLY AND MATCHING ABUTMENT MEMBER (hereafter the "'567 patent").
12. U.S. Pat. No. 5,199,873 issued to Schulte et al. on Apr. 6, 1993 for DENTAL IMPLANT (hereafter the "'873 patent").
13. U.S. Pat. No. 5,100,323 issued to Friedman et al. on Mar. 31, 1992 for DENTAL IMPLANT (hereafter the "'323 patent").
14. U.S. Pat. No. 5,695,336 issued to Lazzara et al. on Dec. 9, 1997 for DENTAL IMPLANT FIXTURE FOR ANCHORAGE IN CORTICAL BONE (hereafter the "'336 patent").
15. U.S. Pat. No. 5,702,346 issued to Lazzara et al. on Dec. 30, 1997 for DENTAL IMPLANT FIXTURE FOR ANCHORAGE IN CORTICAL BONE (hereafter the "'346 patent").
16. U.S. Pat. No. 5,709,547 issued to Lazzara et al. on Jan. 20, 1997 FOR DENTAL IMPLANT FOR ANCHORAGE IN CORTICAL BONE (hereafter the "'547 patent").
17. U.S. Pat. No. 5,727,943 issued to Beaty et al. on Mar. 17, 1998 for SELF-TAPPING, SCREW-TYPE DENTAL IMPLANT" (hereafter the "'943 patent").
18. U.S. Pat. No. 5,607,480 issued to Beaty on Mar. 4, 1997 for SURGICALLY IMPLANTABLE PROSTHETIC DEVICES (hereafter the "'480 patent").
19. U.S. Pat. No. 4,252,525 issued to Child on Feb. 24, 1981 for DENTAL IMPLANT (hereafter the "'525 patent").
20. U.S. Pat. No. 4,531,916 issued to Scantlebury et al. on Jul. 30, 1985 for DENTAL IMPLANT WITH EXPANDED PTFE GINGIVAL INTERFACE (hereafter the "'916 patent").
21. U.S. Pat. No. 4,768,956 issued to Kurpis on Sep. 6, 1988 for DENTAL IMPLANT (hereafter the "'956 patent").
22. U.S. Pat. No. 4,997,383 issued to Weiss et al. on Mar. 5, 1991 for DENTAL IMPLANT (hereafter the "'383 patent").
23. U.S. Pat. No. 5,006,068 issued to Lee et al. on Apr. 9, 1991 for DENTAL IMPLANT (hereafter the "'068 patent).
24. U.S. Pat. No. 5,007,835 issued to Valen on Apr. 16, 1991 for DENTAL IMPLANT (hereafter the "'835 patent).
25. U.S. Pat. No. 5,174,755 issued to Fukuda on Dec. 29, 1992 for DENTAL IMPLANT (hereafter the "'755 patent").
26. U.S. Pat. No. 5,316,476 issued to Krauser on May 31, 1994 for DENTAL IMPLANT WITH A LONGITUDINALLY GROOVED CYLINDRICAL SURFACE (hereafter the "'476 patent").
27. U.S. Pat. No. 5,376,004 issued to Mena on Dec. 27, 1994 for DENTAL IMPLANT DEVICE (hereafter the "'004 patent").
28. U.S. Pat. No. 5,399,090 issued to Padros-Fradera on Mar. 21, 1995 for DENTAL IMPLANT (hereafter the "'090 patent").
29. U.S. Pat. No. 5,425,639 issued to Anders on Jun. 20, 1995 for DENTAL IMPLANT WITH SHOCK ABSORBENT CUSHIONED INTERFACE (hereafter the "'639 patent").
30. U.S. Pat. No. 5,489,210 issued to Hanosh on Feb. 6, 1996 for EXPANDING DENTAL IMPLANT AND METHOD FOR ITS USE (hereafter the "'210 patent").
31. U.S. Pat. No. 5,725,377 issued to Lemler et al. on Mar. 10, 1998 for DENTAL IMPLANT APPARATUS (hereafter the "'377 patent").
32. U.S. Pat. No. 5,492,470 issued to Anders on Feb. 20, 1996 for DENTAL IMPLANT WITH SHOCK ABSORBENT CUSHIONED INTERFACE (hereafter the "'470 patent").
33. U.S. Pat. No. 5,533,898 issued to Mena on Jul. 9, 1996 for DENTAL IMPLANT DEVICE (hereafter the "'898 patent").
34. U.S. Pat. No. 5,564,925 issued to Shampanier on Oct. 15, 1996 for IMPLANT FOR AN ARTIFICIAL TOOTH (hereafter the "'925 patent").
35. U.S. Pat. No. 5,584,693 issued to Nishihara on Dec. 17, 1996 for ARTIFICIAL DENTAL ROOT (hereafter "'693 patent").

36. U.S. Pat. No. 5,601,429 issued to Blacklock on Feb. 11, 1997 for DENTAL IMPLANT ANCHOR (hereafter the "'429 patent").
37. U.S. Pat. No. 5,611,688 issued to Hanosh on Mar. 18, 1997 for EXPANDING DENTAL IMPLANT AND METHOD FOR ITS USE (hereafter the "'688 patent").
38. U.S. Pat. No. 5,636,989 issued to Somborac et al. on Jun. 10, 1997 for DENTAL IMPLANT (hereafter the "'989 patent").
39. U.S. Pat. No. 5,658,146 issued to Kisielewski et al. on Aug. 19, 1997 for DENTAL IMPLANT (hereafter the "'146 patent").
40. U.S. Pat. No. 5,695,335 issued to Haas et al. on Dec. 9, 1997 for DENTAL IMPLANT (hereafter the "'335 patent").
41. U.S. Pat. No. 5,704,788 issued to Milne on Jan. 6, 1998 for DENTAL IMPLANT ABUTMENT SCREW LOCK (hereafter the "'788 patent").

None of the cited patents disclose the concept of creating an entire implant which has the general configuration of the specific tooth. The '370 patent discloses a generally cylindrical implant which then expands into a main body which can be triangular in shape, round in shape, or rectangular in shape. The '526 patent discloses a dental implant that is preformed, having a general conical taper to reflect the average taper of a single rooted tooth. The '152 patent discloses a dental implant that is shaped like a bottle. The '659 patent discloses a dental implant with a cylindrical body and attachments thereto. The '607 patent discloses a dental implant including a body portion having a first external wall portion carrying one or more circumferential projections separated by circumferential grooves and a second external wall portion carrying threads. The '381 patent discloses a screw-type dental implant anchor which includes an externally-threaded body portion having internal structure for engaging an insertion tool. The '181 patent discloses a dental implant including a body portion having a first external wall portion carrying one or more circumferential projections separated by circumferential grooves and a second external wall portion carrying threads. The '016 patent discloses a cylindrical implant with external threads and attachments to the implant.

The '230 patent discloses a dental implant with a hollow bottom sleeve that can be split into multiple segments and an expander. The '372 patent discloses a dental implant with a cylindrical implant having a reinforced healing cap and abutment. The '567 patent discloses a dental implant with a cylindrical implant which has various shaped healing caps attached thereto to accommodate specific tooth shapes. The '873 patent discloses an implant with a cylindrical post and a replacement tooth head fastenable to the post. The '323 patent discloses a dental implant with a cylindrical body. The '336 patent discloses a dental implant with a cylindrical body. The '346 patent discloses a dental implant with a cylindrical body. The '547 patent discloses a dental implant with a cylindrical body. The '943 patent discloses a self-tapping implant having a cylindrical body with a threaded surface. The '480 patent discloses an implant wherein the surface of the implant is impacted with particles of the same material as the device to form the surface into a desired pattern of roughness.

The '525 patent discloses an implant having a cylindrical body and grooves along its outer surface. The '916 patent discloses a dental implant having a cylindrical body. The '956 patent discloses a dental implant of cylindrical shape and an unusual supporting structure. The '383 patent discloses a dental implant which is specifically designed to properly distribute the forces exerted on the bone by the implant. The '068 patent discloses a dental implant with a cylindrical body and attachments thereto. The '835 patent discloses a dental implant with a cylindrical generally screw-shaped body. The '755 patent discloses a dental implant with a cylindrical body wherein the stress absorbing member is made of super elastic material. The '476 patent discloses a dental implant with a cylindrical body. The '004 patent discloses a dental implant with a cylindrical body and further having beveled portions.

The '090 patent discloses a dental implant which includes a main body having a protuberance with a polygonal cross-section. The '090 patent discloses a dental implant with a cylindrical body. The '210 patent discloses an implant with a threaded cylindrical body and designed to receive a threaded expander screw. The '377 patent discloses an implant with a threaded cylindrical body and a bone growth stimulator. The '470 patent discloses a dental implant with a cylindrical body. The '898 patent discloses a dental implant with a beveled portion. The '925 patent discloses a dental implant with convex and concave surfaces. The '693 patent discloses a dental implant with inner and outer root portions. The '429 patent discloses an implant having tapering threads on its external surface. The '688 patent discloses a dental implant with a threaded exterior surface which can also receive an expander screw. The '989 patent discloses an implant having a tapered apical portion and a keyway. The '146 patent discloses a dental implant with a cylindrical body and a threaded free end. The '335 patent discloses a dental implant having a threaded generally cylindrical body. The '788 patent discloses a dental implant having a generally cylindrical body with attachments thereto.

SUMMARY OF THE PRESENT INVENTION

The present invention is a complete truly anatomical dental implant system to replace missing teeth in both the maxillary and mandibular arch. The primary uniqueness of the present invention is in the creation of a unique dental implant that is placed into the jawbone. In previous dental implants that bore into bone to support a prosthesis (i.e. a tooth), the dental implants have been round in shape. Teeth are not round but have distinctive shapes, triangular for anteriors (front) and oval for posteriors (back). The present invention involves and exposes a new procedure, method and apparatus for creating a truly tooth shaped cavity into the jawbone which matches the unique tooth shaped implant, thereby providing a much more stabile base on which to place an abutment and or prosthesis.

It has been discovered, according to the present invention, that if a tooth shaped implant having an overall shape and cross-section of a natural tooth is implanted into the alveolus of a jawbone, then the implant provides a much stronger, firmer, and more secure base on which to mount a healing cap and abutment member and which conforms to match the shape of the natural tooth which is being replaced.

It has also been discovered, according to the present invention, that utilization of a cutting tool bit which is manufactured into the shape of the implant chosen to replace a given tooth and impregnated with cutting means such as diamonds, combined with the utilization of ultrasonics (oscillating or vibrating), enables a practitioner to cut the exact tooth shape into the alveolus of the jawbone to exactly fit the tooth shaped implant of the present invention.

It has also been discovered, according to the present invention, that utilization of a tooth shaped implant enables the practitioner to utilize a tooth color abutment and tooth shaped abutment that projects through the tissue and allows placement of a prosthesis which is much more natural looking than prior art prostheses, and is far more aesthetically desirable than prior art abutments.

Previous titanium implants were round because of ease of manufacturing and ease of placement. Current systems for placing round dental implants consist of drilling a round hole in the patient's bone and either pressing or screwing them into position. It has further been discovered, according to the present invention, that utilization of a tooth shaped instrument which is impregnated with cutting means enables the practitioner to cut an exactly conforming non-round hole in the bone which can then accommodate the tooth shaped non-round implant.

It has also been discovered, according to the present invention, that the key to using anatomical (true tooth shaped) titanium dental implants is to provide a drilling/cutting instrument to enable the clinician to cut a non-round shape in the jawbone and thus obtain primary stability during placement. The surgeon placing the implant would use a standard drilling technique to a particular point and then finish the osteotomy with an ultrasonic attachment (or alternative means such as a vibrating or oscillating attachment), anatomically shaped (the shape of the individual implant) and impregnated with small cutting granules of diamond, tungsten, carbide, or similar appropriate materials (particles) for efficient cutting. This will provide proper primary stability at placement, which will allow the use of an anatomical shape.

It is therefore an object of the present invention to provide a method and apparatus for restoring a patient's missing teeth with a truly tooth shaped titanium dental implant to thereby allow the dentist to restore the missing tooth/teeth with a prosthesis that more closely matches the natural dentition.

It is an additional object of the present invention to address the problem inherent in prior art implants which utilize a round shape. The round shape of prior implants creates the problem of trying to make the round implant look like real teeth that are not round in shape. The present invention addresses this problem by creating a tooth shaped implant that more closely matches the shape of the specific tooth which has been extracted, to provide a stronger supporting base and make the replacement tooth far more natural looking.

It is a further object of the present invention to provide titanium dental implants of different shapes to match different teeth. The implant is small and large tapered essentially triangular in shape respectively for both small and large anterior teeth. The implant is tapered essentially oval in shape for cuspid and bicuspid teeth. The implant is large tapered essentially oval-rectangular in shape for molar teeth. The connecting top (table) of the implant would be tooth shaped with a slightly taller than standard external hex design (1 mm tall and 2.7 mm between flat of hex) for antirotation and connection of the abutment and or prosthesis. The hex would be designed with a circumferential depression area at the junction of the hex to the table for the placement of a sealing ring. In addition, the implant could be fabricated with a connecting device such as an internal hex or some type of tapered internal connective device such as a morris taper, etc.

It is also an object of the present invention to provide tooth shaped implants which can be press fit into pre-drilled tooth shaped holes. The present invention implant would be a press fit design with either a polished titanium collar or porcelain collar extension apical to the table top, with a tapered polished surface to contact the coronal cortical bone which extends apical to the collar. The principal bone contact area of the implant would be fabricated with an irregular surface pretreated with an acid etch or similar technique (bone inductive or conductive materials), to create surface roughness for the purpose to enhance bone contact. In addition, the implant could also be fabricated with a variety of surface textures such as plasma spray, HA (Hydroxy Apetite) coating, etc. It is also within the spirit and scope of the present invention to have a smooth, threadlike or stepped surface design.

It is an additional object of the present invention to have a natural tooth shaped implant which can accommodate either a one-stage (one surgery) or two-stage (two surgeries) technique. The one stage technique reduces the number of surgeries the patient must undergo.

It is a further object of the present invention to provide a tooth shaped implant which can be immediately placed in extraction sites. The collar of the implant can be made of either metal (titanium) or a ceramic type (ceramic or other tooth colored material) of tooth color material. This would allow the implant to be placed in immediate extraction sites and allow for any resorption of bone and soft tissue that might expose the table of the implant. This ceramic type material could be prepared and would provide a tooth colored foundation for a ceramic prosthesis and would result in improved aesthetic results which accurately match the patient's missing tooth and adjacent teeth.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of the present invention tapered rounded triangular shaped dental implant.

FIG. 2 is a cross-sectional view taken along line 2—2 of FIG. 1.

FIG. 3 is a top plan view of the present invention rounded triangular shaped dental implant.

FIG. 4 is a perspective view of the present invention tapered oval-shaped dental implant.

FIG. 5 is a cross-sectional view taken along line 5—5 of FIG. 4.

FIG. 6 is a top plan view of the present invention tapered oval-shaped dental implant.

FIG. 7 is a perspective view of the present invention tapered oval-rectangular shaped dental implant.

FIG. 8 is a cross-sectional view taken along line 8—8 of FIG. 7.

FIG. 9 is a top plan view of the present invention tapered oval-rectangular shaped dental implant.

FIG. 17 is an illustration of one tool which can be used to perform the operation depicted in FIG. 16.

FIG. 18 is an illustration of another tool which can be used to perform the operation depicted in FIG. 16.

DESCRIPTION OF THE PREFERRED EMBODIMENT

Figure 10:
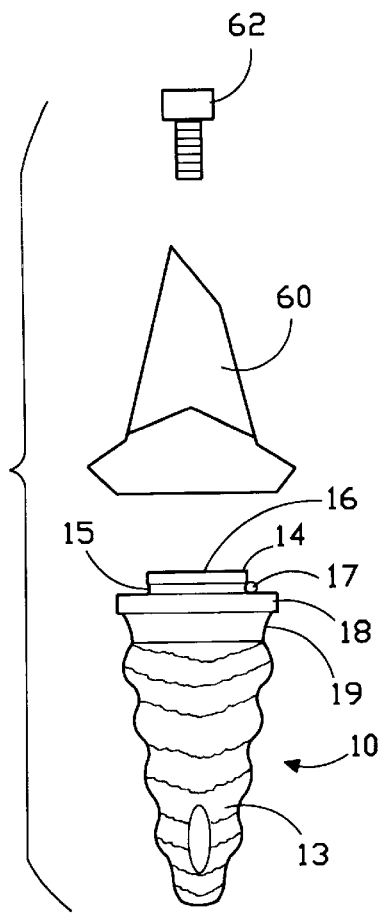
FIG. 10 is an exploded view of the present invention rounded tapered triangular shaped implant utilized with an abutment for anterior teeth.

Although specific embodiments of the present invention will now be described with reference to the drawings, it should be understood that such embodiments are by way of example only and merely illustrative of but a small number of many specific embodiments which can represent applications of the principles of the present invention. Various changes and modifications obvious to one skilled in the art to which the invention pertains are deemed to be within the spirit, scope and contemplation of the present invention as further defined in the appended claims.

Referring to FIGS. 1, 2, and 3, there is illustrated respectively a perspective view, a cross-sectional view and a top plan view of the present invention tapered rounded triangular shaped dental implant 10 which is used for both small and large anterior teeth. The novel feature of the present invention is that the entire tapering cross-section of the present invention implant 10 from the top surface 12 to the apex 15 is tapered rounded triangular in shape, comparable to the top surface or table 12 as shown. Therefore, the dental implant 10 is designed to conform to the shape of the specific teeth so that it provides a full natural support for the tooth analogue. The dental implant illustrated in FIGS. 1, 2 and 3 is shown with an external hex 14 as the connecting member to the abutment. It will be appreciated that the member can also be an internal hex or any other connecting device well known in the art such as a Morris taper. The hex 14 rests on top of the table or collar 18 having the surface 12 onto which the abutment is placed. The hex 14 is preferably also designed with a circumferential depression 15 to accommodate the placement of a sealing ring 17 into the circumferential depression 15. The collar 12 rests on a tapering area 9 which extends into the body of the implant 19. As illustrated in FIG. 1, the body of the implant has an irregular surface 13 which has surface roughness to enhance bone contact. The surface roughness is achieved by pretreating the surface with acid etch or similar techniques. The implant is preferably made of strong material such as titanium. The entire cross-section along the length of the implant is rounded triangular in shape. The implant 10 also has internal threads 16 which are designed to accommodate a threaded screw or bolt. The threaded screw or bolt attaches an abutment to the implant. Referring to conventional dental tooth numbering, the tapered rounded triangular shaped implant is used for anterior teeth numbers 7, 8, 9, 10, 23, 24, 25, and 26. It may also be used for cuspid teeth number 6, 11, 22 and 27.

Referring to FIGS. 4, 5 and 6, there are illustrated respectively a perspective view, a cross-sectional view and a top plan view of the present invention tapered oval-shaped dental implant 20 which is used for both cuspid and bicuspid teeth. If there is not sufficient bone width at a molar location, then this can also be used for molars. The novel feature of the present invention is that the entire tapering cross-section of the present invention implant 20 from the top surface 22 to the apex 25 is tapered oval in shape, comparable to the top surface or table 22 as shown. Therefore, the dental implant 20 is designed to conform to the shape of the specific teeth so that it provides a full natural support for the tooth analogue. The dental implant illustrated in FIGS. 4, 5 and 6 is shown with an external hex 24 as the connecting member to the healing abutment. It will be appreciated that the member can also be an internal hex or any other connecting device well known in the art such as a Morris taper. The hex 24 rests on top of the table or collar 28 having top surface 22 onto which the abutment is placed. The hex 24 is preferably also designed with a circumferential depression 25 to accommodate the placement of a sealing ring 27 into the circumferential depression 25. The collar 28 rests on a tapering area 29 which extends into the body of the implant 31. As illustrated in FIG. 4, the body of the implant has an irregular surface 33 which has surface roughness to enhance bone contact. The surface roughness is achieved by pretreating the surface with acid etch or similar techniques. The implant is preferably made of strong metal such as titanium. The entire cross-section along the length of the implant is generally oval in shape. The implant 20 also has internal threads 26 which are designed to accommodate a threaded screw or bolt. The threaded screw or bolt attaches an abutment to the implant. Referring to conventional dental tooth numbering, the small tapered oval-shaped implant is used for bicuspid teeth numbers 4, 5, 12, 13, 20, 21, 28, and 29. In some cases, it may also be used for molar locations when indicated by the smaller size of the molars on a particular individual's teeth. It may also be used for cuspid teeth numbers 6, 11, 22 and 27.

Referring to FIGS. 7, 8 and 9, there are illustrated respectively a perspective view, a cross-sectional view and a top plan view of the present invention tapered oval-rectangular shaped dental implant 50 which is used for molar teeth when adequate bone width is present. The novel feature of the present invention is that the entire tapering cross-section of the present invention implant 50 from the top surface 52 to the apex 55 is oval-rectangular in shape, comparable to the top surface or table 52 as shown. Therefore, the dental implant 50 is designed to conform to the shape of the specific teeth so that it provides a full natural support for the tooth analog. The dental implant illustrated in FIGS. 7, 8 and 9 is shown with an external hex 54 as the connecting member to the healing abutment. It will be appreciated that the member can also be an internal hex or any other connecting device well known in the art such as a Morris taper. The hex 54 rests on top of the table or collar 58 having top surface 52 onto which the abutment is placed. The hex 54 is preferably also designed with a circumferential depression 55 to accommodate the placement of a sealing ring 57 into the circumferential depression 55. The collar 58 rests on a tapering area 59 which extends onto the body of the implant 49. As illustrated in FIG. 7, the body of the implant has an irregular surface 47 which has surface roughness to enhance bone contact. The surface roughness is enhanced by pretreating the surface with acid etch or similar techniques. The implant is preferably made of strong metal such as titanium. The entire cross-section along the length of the implant is generally oval-rectangular in shape. The implant 50 also has internal threads 56 which are designed to accommodate a threaded screw or bolt. The threaded screw or bolt attaches an abutment to the implant. Referring to conventional dental tooth numbering, the large oval-shaped implant is used for upper molar teeth numbers 2, 3, 14, and 15 and for lower molar teeth numbers 18, 19, 30 and 31.

An exploded view of the present invention rounded triangular shaped implant utilized with conventional attachment members is illustrated in FIG. 10. The implant 10 is preferably made of dental titanium or other suitable biocompatible material. The implant's surface 13 would be made of standard commercial finishes and would be plasma sprayed, acid etched, HA coated, etc. While the implant is illustrated with a generally smooth surface, it will be appreciated that the surface could also be threaded as is well known in the art and also could be stepped as is also well known in the art. The implant 10 has a collar 18 adjacent its top surface. The collar 18 is to be fabricated with either a polished titanium material or preferably a new ceramic colored material to more properly match the tooth color of the replacement tooth analogue. Apical to the collar is a tapered smooth surface 19 as previously discussed.

When utilized with a conventional two-stage method, after the implant 10 is inserted into the jawbone, a cover screw is attached to the top of the implant with a standard metal hex bolt and the cover screw allows the gingival tissues to heal. The cover screw is fitted onto a conventional connecting member, which in the present case is illustrated as a standard external hex 14. Alternatively, the present invention can accommodate an internal hex, an internal device such as Morris taper, and other conventional connecting means. The threads on the bolt are threaded into the internal thread 16 of rounded triangular shaped implant 10.

Figure 11:
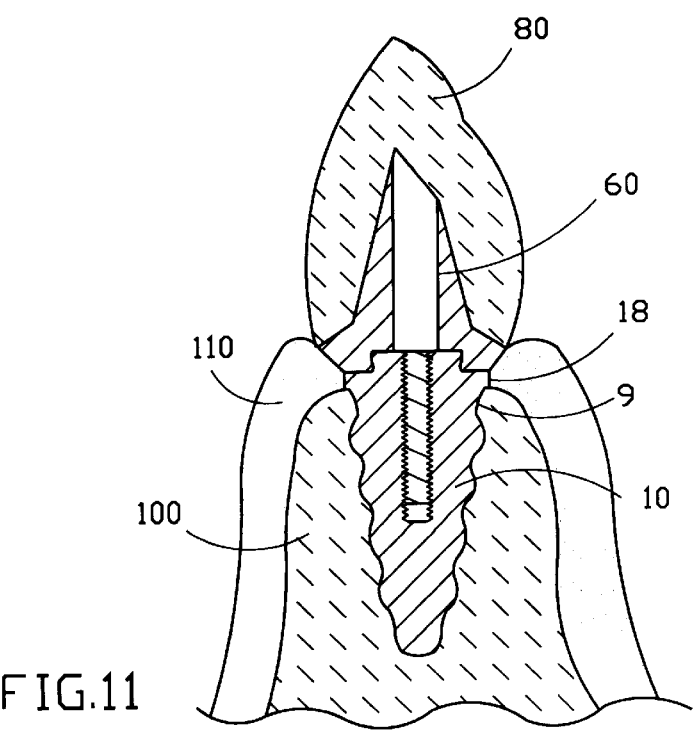
FIG. 11 is a cross-sectional view of the present invention rounded tapered triangular shaped implant with abutment and an anterior tooth cemented to the abutment in place embedded into soft tissue and bone.

After a sufficient healing period, the cover screw is removed and replaced with a healing cap which is attached to a threaded bolt whose threads are threaded into the internal thread 16. Since the tapered rounded triangular implant 10 is used, then the top surface of the healing cap would be rounded triangular in shape. Final impressions to the implant are taken and the selected abutment is secured with a standard bolt. Illustrated in FIG. 10, the abutment 60 is then attached to the implant with a threaded bolt 62, which threads extend into the internal thread 16. Referring to FIG. 11, the final implant is shown in place. Here, the implant 10 has been imbedded in bone 100 and soft tissue 110 such that the implant itself extends into the bone 100 while the collar abuts the soft tissue 110 and the abutment 60 rests immediately on top of the implant as shown. Since the surface of the abutment is tapered rounded triangular in shape for proper alignment with an anterior tooth, the surface which is rounded triangular in shape fits perfectly with the present rounded triangular shaped implant. A replacement tooth analogue (prosthesis 80) for an anterior tooth is then attached to said abutment by means of a threaded bolt or by cement. In the illustration in FIG. 11 it is attached by cement. Since the entire implant 10 is rounded triangular in cross-section, it simulates the natural root of an anterior tooth and therefore provides a much more secure surface, stable and better support for the anterior tooth analogue. The roughened surface of the implant further provides more bone contact area to facilitate the bone 100 growing into the depressions in the roughened surface to make for a much more strong secure fit.

Figure 12:
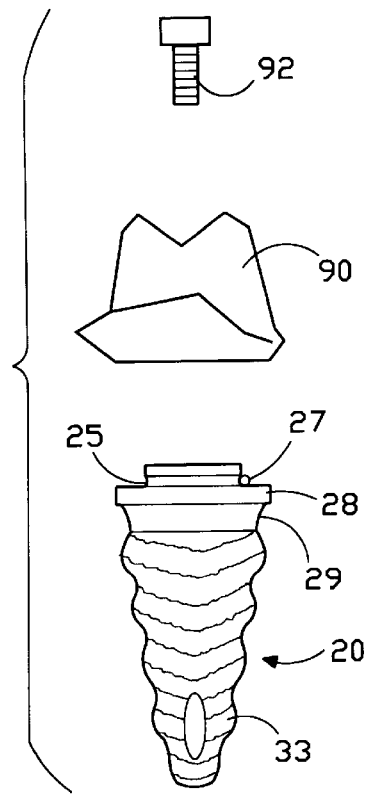
FIG. 12 is an exploded view of the present invention tapered oval or oval-rectangular shaped implant utilized with an abutment for cuspid, bicuspid and molar teeth.
Figure 13:
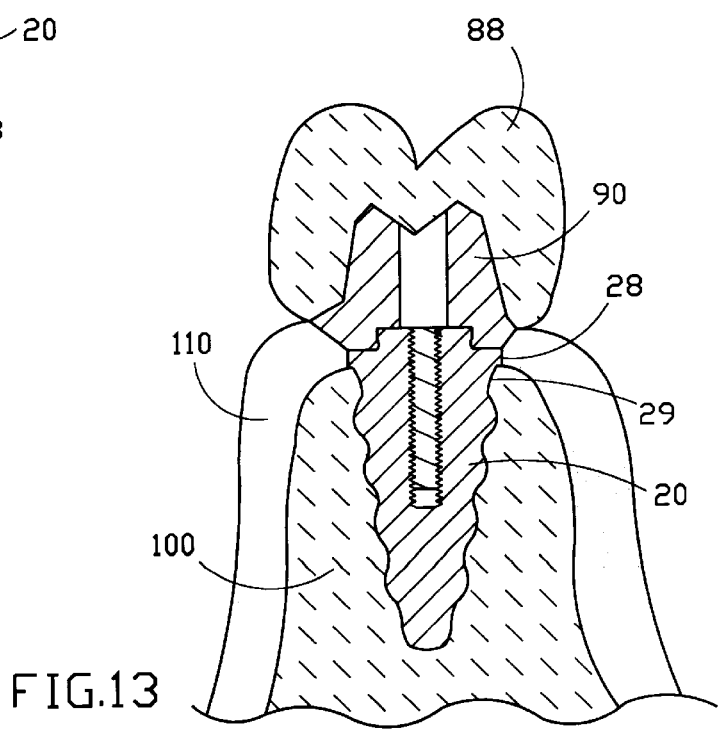
FIG. 13 is a cross-sectional view of the present invention tapered oval or oval-rectangular shaped implant with abutment and a bicuspid tooth cemented to the abutment in place embedded into soft tissue and bone.

Referring to FIGS. 12 and 13, comparable exploded views and cross-sectional views of a final implant imbedded into the alveolus of a jawbone for use with an oval or oval-rectangular shaped implant is shown. The specific implant shown in FIGS. 12 and 13 is the oval-shaped implant but it will be appreciated that the same views could be used to illustrate an oval-rectangular shaped implant with a different tooth analogue. Once again, after the healing period has been completed with the cover screw and the healing cap if required, the final abutment 90 is set in place on the oval-shaped implant 20 and attached with a bolt 92 which is threaded into internal threads 26. Once again, the implant 20 is imbedded into the bone 100. The roughened surface 33 provides areas for the bone to grow into the implant to make for a secure fit. The cuspid or bicuspid tooth 88 which has a generally oval cross-section now fits onto the matching oval cross-sectional shape implant 20. The tooth analogue to replace cuspids and bicuspids is oval in shape and would be a perfect fit. Since the entire implant 20 is small, tapered oval in cross-section, it simulates the natural root of a cuspid and bicuspid tooth and therefore provides a much more secure, stable and better support for the cuspid and bicuspid tooth analogue (prosthesis).

Similarly, if the oval-rectangular implant 50 were utilized in FIGS. 12 and 13, then the top surface 52 and collar 58 would be oval-rectangular in shape. The tooth analogue to replace molars would be oval-rectangular in shape and would be a perfect fit. Since the entire implant 50 is tapered oval-rectangular in cross-section, it simulates the natural root of a molar tooth and therefore provides a much more secure, stable and better support for the molar tooth analogue.

The inventor of the present invention has discovered that a key to making the tooth shaped implants work is to have a drilling system that will allow the clinician to cut a non-round hole (tooth shaped) into the jawbone. An important criterion for success with dental implants is that the implant must be solidly secured during placement with no movement of the implant fixture in the bone.

In the art for round implants, the traditional and current technique is to drill a round hole and either press fit or screw a round titanium implant solidly into position. The implant would then heal for four to six months. The technique discovered for utilization of the present invention tooth shaped implant is to first use the conventional drilling technique utilizing round tapered drill bits and then finish the drilling with an ultrasonic broaching (vibrating, oscillating) action having a bur impregnated with small cutting granules of diamond, tungsten carbide, or similar appropriate materials (particles) for efficient cutting and that is shaped like the actual implant fixture that will be press fit into the patient's jawbone. The final shape of the bone socket (osteotomy) shape is accomplished by a reciprocating, oscillating, vibrating, ultrasonic, filing or broaching action rather than a revolving turning rotating action.

Figure 14:
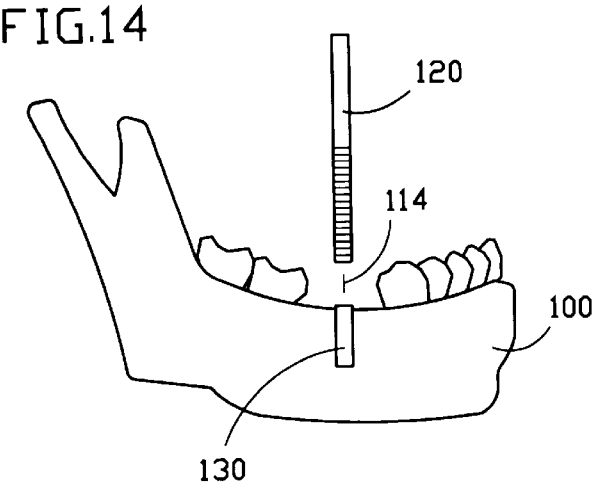
FIG. 14 is an illustration of the initial process for implanting the present invention dental implant in a jawbone utilizing a round drill to drill a round hole.
Figure 15:
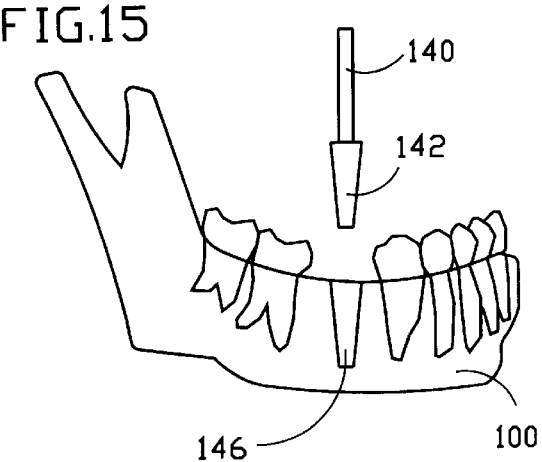
FIG. 15 is an illustration of the intermediate process for implanting the present invention dental implant in a jawbone utilizing a truncated pyramid to continue the hole.
Figure 16:
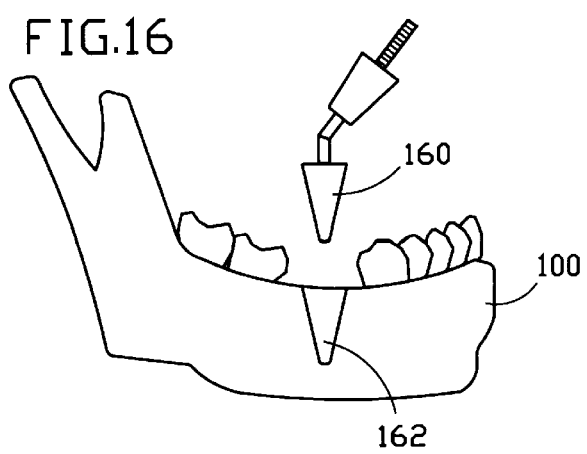
FIG. 16 is an illustration of the third step process for implanting the present invention dental implant in a jawbone utilizing a special bur shaped in the form of the dental implant.

The method for implanting the present invention tooth shaped implant into a patient's jawbone is illustrated in FIGS. 14 through 16. The initial portion of the process is illustrated in FIG. 14. The location of the missing tooth site 114 is located and a conventional round tapered drill 120 is used to drill a round hole 130 into the patient's jawbone 100. As an optional intermediate step, before the final broaching bur is utilized, referring to FIG. 15, a second tool 140 having a truncated triangular-shaped head 142 is used to create a generally truncated shape cavity 146 in the patient's jawbone 100 which is very similar to the final shape that will be desired. It is believed that this intermediate step will facilitate the final last stage. It is also emphasized, however, that depending upon the size of the cavity, the process can go directly from the rounded hole as illustrated in FIG. 14 into the final wedge shape hole as illustrated in FIG. 16. Referring to FIG. 16, the present invention includes having cutting bur 160 as the final stage of cutting which is exactly the same size and shape as the tooth implant to be placed into the completely drilled opening. Depending on the circumstances, either the round hole 130 has already been pre-drilled into the opening or the truncated hole 146 has then been drilled into the opening after the initial round hole has been drilled. Finally, what remains is to have the specially shaped bur to complete the formation of a tooth shaped opening 162 in the jawbone 100. The bur 160 is driven by ultrasonics so that the cutting metal impregnated surface which may be a diamond impregnated surface cuts the jawbone to exactly the same shape as the tooth shaped bur 160. Through this ultrasonic action, the opening 162 is formed in exactly the same shape as the tooth shaped implant. The difference between the surface of the cut 162 and the tooth shaped implant is that the surface will be generally smooth. This facilitates a snug fit with the roughened surface implant being press-fitted into the opening 162 which is generally of the same shape but has the smooth surface. While there initially will be some cavities, the bone will grow into the cavities in the roughened surface to enhance the strength of the fixture of the implant into the jawbone.

Referring to FIG. 11, the tooth shaped implant 10 is then press fit into the opening 162 to exactly match the opening created by the exact same shaped bur 160. In this case the tapered rounded triangular shaped implant 10 from FIG. 1 is illustrated in FIG. 11. Similarly, referring to FIG. 13, the generally oval-shaped implant has been press fitted into the formed cavity 162 in the jawbone. It will be appreciate that the same technique can be used for the oval-rectangular shaped implant discussed in FIGS. 7 through 9 for a molar. Referring to FIGS. 11 and 13, the tapered portions 9 and 29 below their respective collars is shown resting on the surface of the bone so that after a tooth analogue is fitted onto the abutment, the collar 18 or 28 respectively which rests adjacent a gumline or bone may or may not be visible. By having the collar (18 or 28 respectively) made of ceramic tooth-colored material, the overall cosmetic appearance will be substantially improved.

One tool which can be used to perform the operation depicted in FIG. 16 is illustrated in FIG. 17. This tool is an ultrasonic scaler 340 as illustrated in FIG. 17. An ultrasonic scaler unit connected to an AC power source 350 is used. A sterile water line 310 feeds sterile water from a sterile water source 320 through a peristaltic pump and out to a housing member 330 to drive the bur 142 and to prevent overheating of the bone during cutting. This is used when a source of compressed air is not available.

An alternative tool for performing the above task is illustrated in FIG. 18. The clinician can use a Kavo Sonicflex Ultrasonic Handpiece 200 or similar device. This handpiece 200 is driven by compressed air. A sterile water line 210 provides sterile water from a sterile water source 220 which is used to drive the bur 160. The surface and tip of the bur 160 is impregnated with a hard material such as diamonds for efficient cutting.

Figure 19:
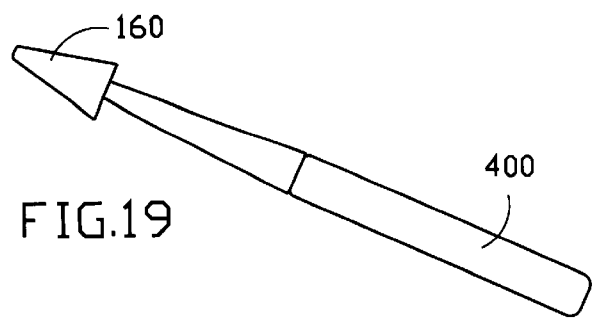
FIG. 19 is an illustration of a hand tool incorporating the bur utilized to finalize the shape of the hole in the jawbone designed to receive the present invention dental implant.

Finally, referring to FIG. 19, a hand held piece 400 with a bur 160 at its tip can be used. These hand held osteotomes are used to help condense and contour the bone to the desired shape and would be made at different angles. The instrument 400 can be used with a mallet to tap the bur 160 into place. The tool will also help to expand the jawbone. This hand held tool is generally only used for the maxillary arch but could be used at any location.

Of course the present invention is not intended to be restricted to any particular form or arrangement, or any specific embodiment disclosed herein, or any specific use, since the same may be modified in various particulars or relations without departing from the spirit or scope of the claim invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing fall public disclosure of at least one of its forms. However, such detailed description is not intended in any way to limit the broad features or principles of the present invention, or the scope of patent monopoly to be granted.

What is claimed is:

1. A dental implant to be implanted into a jawbone to support an abutment and tooth analogue in the shape of an anterior tooth to replace an anterior tooth, comprising:

a. a tapered rounded triangular-shaped implant having an exterior surface, a collar with a top surface, and configured to taper from the collar to an apex wherein the general cross-section of the implant from the collar to its apex is rounded triangular shape in cross-section;

b. the rounded triangular shaped implant for being embedded into a precut opening in the jawbone wherein the precut opening is the same shape as the rounded triangular shaped implant so that the rounded triangular shaped implant is for being press fitted into the opening with the apex located deepest into the jawbone and the collar is adjacent a gumline or bone; and c. means for retaining an abutment on the tapered rounded triangular shaped implant and means for retaining the tooth analogue in the shape of an anterior tooth on the abutment;

d. whereby the rounded triangular shaped implant provides an improved structural support and cosmetic fit for the anterior tooth analogue.

2. The dental implant as defined in claim 1 wherein the collar is ceramic tooth colored.

3. The dental implant as defined in claim 1 further comprising internal threads extending from its top surface of the collar into the body of the implant to receive a threaded bolt for attaching at least said abutment to the tapered rounded triangular shaped implant.

4. The dental implant as defined in claim 1 wherein said exterior surface of the dental implant is treated to create a textured surface.

5. The dental implant as defined in claim 1 wherein said exterior surface of the dental implant is threaded.

6. The dental implant as defined in claim 1 wherein said dental implant has a stepped exterior.

7. The dental implant as defined in claim 1 further comprising an exterior hex connection on the top surface of the collar and having a circumferential depression between the hex and the top surface of the collar to accommodate and receive a sealing ring.

8. A dental implant to be implanted into a jawbone to support an abutment and tooth analogue in the shape of a cuspid tooth to replace a cuspid tooth, comprising:

a. a tapered rounded triangular shaped implant having an exterior surface, a collar with a top surface, and configured to taper from the collar to an apex wherein the general cross-section of the implant from its collar to its apex is tapered rounded triangular shape in cross-section;

b. the rounded triangular shaped implant for being embedded into a precut opening in the jawbone wherein the precut opening is the same shape as the rounded triangular shaped implant so that the rounded triangular shaped implant is for being press fitted into the opening with the apex located deepest into the jawbone and the collar is adjacent a gumline or bone; and c. means for retaining an abutment on the rounded triangular shaped implant and means for retaining the tooth analogue in the shape of a cuspid tooth on the abutment;

d. whereby the rounded triangular shaped implant provides an improved structural support and cosmetic fit for the cuspid tooth analogue.

9. The dental implant as defined in claim 8 wherein the collar is ceramic tooth colored.

10. The dental implant as defined in claim 8 further comprising internal threads extending from its top surface of the collar into the body of the implant to receive a threaded bolt for attaching at least said abutment to the tapered rounded triangular shaped implant.

11. The dental implant as defined in claim 8 wherein said exterior surface of the dental implant is treated to create a textured surface.

12. The dental implant as defined in claim 8 wherein said exterior surface of the dental implant is threaded.

13. The dental implant as defined in claim 8 wherein said dental implant has a stepped exterior.

14. The dental implant as defined in claim 8 further comprising an exterior hex connection on the top surface of the collar and having a circumferential depression between the hex and the top surface of the collar to accommodate and receive a sealing ring.

15. A dental implant to be implanted into a jawbone to support an abutment and tooth analogue in the shape of a molar tooth to replace a molar tooth, comprising:

a. a tapered oval-rectangular shaped implant having an exterior surface, a collar with a top surface and configured to taper from the collar to an apex wherein the general cross-section of the implant from its collar to its apex is tapered oval-rectangular shaped in cross-section;

b. the tapered oval-rectangular shaped implant for being embedded into a precut opening in the jawbone wherein the precut opening is the same shape as the tapered oval-rectangular shaped implant so that the tapered oval-rectangular shaped implant is for being press fitted into the opening with the apex located deepest into the jawbone and the collar adjacent a gumline or bone; and c. means for retaining an abutment on the tapered oval-rectangular shaped implant and means for retaining the tooth analogue in the shape of a molar tooth on the abutment;

d. whereby the large tapered oval-rectangular shaped implant provides an improved structural support and cosmetic fit for the molar tooth analogue.

16. The dental implant as defined in claim 15 wherein said collar is ceramic tooth colored.

17. The dental implant as defined in claim 15 further comprising internal threads extending from its top surface of the collar into the body of the implant to receive a threaded bolt for attaching at least said abutment to the large tapered oval-rectangular shaped implant.

18. The dental implant as defined in claim 15 wherein said exterior surface of the dental implant is treated to create a textured surface.

19. The dental implant as defined in claim 15 wherein said exterior surface of the dental implant is threaded.

20. The dental implant as defined in claim 15 wherein said dental implant has a stepped exterior.

21. The dental implant as defined in claim 15 further comprising an exterior hex connection on the top surface of the collar and having a circumferential depression between the hex and the top surface of the collar to accommodate and receive a sealing ring.

22. A dental implant to be implanted into a jawbone to replace an anterior tooth, comprising a tapered rounded triangular shaped implant having an exterior surface, a top surface and configured to taper from the top surface to an apex wherein the general cross-section of the implant from its top surface to its apex is tapered rounded triangular shape in cross-section.

23. A dental implant to be implanted into a jawbone to replace a cuspid tooth, comprising a tapered rounded triangular shaped implant having an exterior surface, a top surface and configured to taper from the top surface to an apex wherein the general cross-section of the implant from its top surface to its apex is tapered rounded triangular shape in cross-section.

24. A dental implant to be implanted into a jawbone to replace a molar tooth, comprising a tapered oval-rectangular shaped implant having an exterior surface, a top surface and configured to taper from the top surface to an apex wherein the general cross-section of the implant from its top surface to its apex is tapered oval-rectangular shape in cross-section.

* * * * *